United States Patent
Schroeder

(10) Patent No.: US 11,109,549 B2
(45) Date of Patent: Sep. 7, 2021

(54) TOMATO VARIETY NUN 00279 TOP

(71) Applicant: NUNHEMS B.V., Nunhem (NL)

(72) Inventor: Steven Schroeder, Lockeford, CA (US)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 16/732,813

(22) Filed: Jan. 2, 2020

(65) Prior Publication Data

US 2020/0137972 A1    May 7, 2020

Related U.S. Application Data

(63) Continuation of application No. 15/923,263, filed on Mar. 16, 2018, now abandoned.

(60) Provisional application No. 62/516,826, filed on Jun. 8, 2017.

(51) Int. Cl.
*A01H 5/08* (2018.01)
*A01H 1/00* (2006.01)
*A01H 6/82* (2018.01)

(52) U.S. Cl.
CPC .......... *A01H 5/08* (2013.01); *A01H 1/00* (2013.01); *A01H 6/825* (2018.05)

(58) Field of Classification Search
None
See application file for complete search history.

(56) References Cited

U.S. PATENT DOCUMENTS 8,940,976 B2    1/2015    Bunn et al.

FOREIGN PATENT DOCUMENTS

| EP | 1428425 A1 | 6/2004 |
|---|---|---|
| WO | 1998024301 A1 | 6/1998 |
| WO | 1999021411 A1 | 5/1999 |
| WO | 2000074468 A1 | 12/2000 |
| WO | 2008143504 A2 | 11/2008 |
| WO | 2013182646 A1 | 12/2013 |
| WO | 2014076249 A1 | 5/2014 |

OTHER PUBLICATIONS

Bhatia, Poonam, et al., Tissue culture studies of tomato (*Lycopersicon esculentum*, Plant Cell, Tissue and Organ Culture, 2004, pp. 1-21, vol. 78.

UPOV (International Union for the Protection of New Varieties and Plants), "Guidelines for the Conduct of Tests for Distinctness, Uniformity and Stability, TG/44/10" (Geneva 2001) upov.int/en/publications/tg-rom/tg044/tg_44_10.pdf.

US Department of Agriculture, Agricultural Marketing Service, Plant Variety Protection Office, Beltsville, MD 20705 "Objective Description of Variety Tomato (*Lycopersicon esculentum* Mill.)", http://www.ams.usda.gov/sites/default/files/media/55-Tomato%20ST-470-55%202015.pdf, Jun. 2015.

Dorais, M. and Papadopoulos, A.P., Greenhouse Tomato Fruit Quality, Horticultural Reviews, 2001, pp. 239-319, vol. 26.

Vos, Pieter, et al., AFLP: a new technique for DNA fingerprinting, Nucleic Acids Research, 1995, pp. 4407-4414, vol. 23, No. 21.

Ince, Ayse Gul, et al., Genetic Relationships Within and Between Capsicum Species, Biochem. Genet., 2010, pp. 83-95, vol. 48.

Vidavsky, Favi and Czosnek, Henryk, Tomato Breeding Lines Resistant and Tolerant to Tomato Yellow Leaf Curl virus issued from Lycopersicon hirsutum, Phytopathology, 1998, pp. 910-914, vol. 88, No. 9.

Wijnker, Erik, et al., Hybrid recreation by reverse breeding in *Arabidopsis thaliana*, Nature Protocols, 2014, pp. 761-772, vol. 9.

*Primary Examiner* — Phuong T Bui
(74) *Attorney, Agent, or Firm* — Arent Fox LLP

(57) ABSTRACT

The invention provides a new and distinct hybrid variety of tomato, NUN 00279 TOP as well as seeds and plants and fruits thereof.

20 Claims, No Drawings

TOMATO VARIETY NUN 00279 TOP

CROSS-REFERENCE TO RELATED APPLICATIONS

The present application is a continuation of U.S. patent application Ser. No. 15/923,263, filed 16 Mar. 2018, now abandoned, which claims the benefit of U.S. Patent Application Ser. No. 62/516,826, filed 8 Jun. 2017, which are incorporated herein by reference in its entirety.

FIELD OF THE INVENTION

The present invention relates to the field of plant breeding and, more specifically, to the development of NUN 00279 TOP (also designated as NUN 00279 or NUN 00279 F1 or NUN 00279 hybrid). The invention further relates to vegetative reproductions of NUN 00279 TOP, methods for tissue culture of NUN 00279 TOP and regenerating a plant from such a tissue culture and also to phenotypic variants of NUN 00279 TOP.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential. One crop species which has been subject to such breeding programs and is of particular value is the tomato.

Tomato (*Solanum lycopersicum* and closely related species) is naturally a diploid and the basic chromosome number of the genus is x=12, most are 2n=2x=24, including the cultivated ones. It originated in the New World and has since become a mayor food crop. In 2012, FAOSTAT estimated world production at over 160 million tonnes.

Tomato cultivars may be grouped by maturity, i.e. the time required from planting the seed to the stage where fruit harvest can occur. Standard maturity classifications include 'early', 'midseason' or late-maturing'. Another classification for tomatoes is the developmental timing of fruit set. 'Determinate' plants grow foliage, then transition into a reproductive phase of flower setting, pollination and fruit development. Consequently, determinant cultivars have a large proportion of the fruit ripen within a short time frame. Growers that harvest only once in a season favor determinant type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange and purple. Additionally, there are multi-colored varieties exemplified by mainly red fruited varieties with green shoulders, and both striped- and variegated-colored fruit. Tomatoes can also be classified by their market. Some varieties are intended for fresh consumption by consumers. These tomatoes require, for example, good storage properties. Other tomato varieties are optimized for the processing industry. Processing tomatoes can be canned whole, canned, diced or chopped, dried, roasted, pasted, pured or concentrated, juiced, frozen, or put into ready-made dishes, for example sauces, stews or soups.

The fruits of tomato plants which are more suitable for processing are generally red colored and have pink to red/crimson fruit flesh.

SUMMARY OF THE INVENTION

In an aspect of the invention, a seed of tomato variety NUN 00279 TOP is provided, wherein a representative sample of said seed will be deposited under Accession Number NCIMB 43684. The invention also provides for a plurality of seeds of NUN 00279 TOP. The tomato seed of NUN 00279 TOP may be provided as an essentially homogeneous population of tomato seed. Therefore, seed of the invention may be defined as forming at least about 97% of the total seed, including at least about 98%, 99% or more of the seed. The population of seed of NUN 00279 TOP may be particularly defined as being essentially free from other seed. The seed population may be grown into plants to provide an essentially homogeneous population of tomato plants according to the invention.

Also encompassed is a plant grown from a seed of tomato variety NUN 00279 TOP and a plant part thereof. In another aspect the invention provides for a hybrid variety of tomato called NUN 00279 TOP. The invention also provides for a progeny of NUN 00279 TOP. Especially, a plant or a progeny retaining all or all but one, two or three of the "distinguishing characteristics" or all or all but one, two or three of the "morphological and physiological characteristics" of NUN 00279 TOP referred to herein, is encompassed herein as well as methods for producing that plant or progeny.

In one aspect, a plant or a progeny of the invention have all the physiological and morphological characteristics of variety NUN 00279 TOP when grown under the same environmental conditions. In another aspect such a plant or such progeny have all or all but one, two or three of the physiological and morphological characteristics of NUN 00279 TOP when measured under the same environmental conditions and evaluated at significance levels of 1%, 5% or 10% significance (which can also be expressed as a p-value) wherein a representative sample of seed of variety NUN 00279 TOP will be deposited under Accession Number NCIMB 43684. In a second aspect, a plant or a progeny of the invention have all the physiological and morphological characteristics of variety NUN 00279 TOP when grown under the same environmental conditions. In another aspect such a plant or such progeny have all or all but one, two or three of the physiological and morphological characteristics as listed in Table 1 and/or 2 for variety NUN 00279 TOP when measured under the same environmental conditions and evaluated at significance levels of 1%, 5% or 10% significance.

In another aspect a plant of NUN 00279 TOP or said progeny plants has 7, 8, or more or all of the distinguishing characteristics: 1) Average fruit diameter at widest point; 2) Average fruit weight; 3) Typical fruit shape; 4) Average number of flowers in inflorescence; 5) Typical leaf morphology; 6) Average mature plant height; 7) Fruit epidermis type; 8) Average fruit pericarp thickness; 9 Average fruit soluble solids; and 10) Average maturity. NUN 00279 TOP is a processing tomato.

Also a plant part obtained from variety NUN 00279 TOP is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. In a further embodiment, the plant part obtained from variety NUN 00279 TOP is a cell, optionally a cell in a cell or tissue culture. That cell may be grown into a plant of NUN 00279 TOP.

The invention also provides a cell culture of NUN 00279 TOP and a plant regenerated from NUN 00279 TOP, which plant has all the characteristics of NUN 00279 TOP when grown under the same environmental conditions, as well as methods for regenerating NUN 00279 TOP. Alternatively, a regenerated plant may have one characteristic that is different from NUN 00279 TOP.

Further, a vegetatively propagated plant of variety NUN 00279 TOP is provided having all or all but one, two or three of the morphological and physiological characteristics NUN 00279 TOP when grown under the same environmental conditions.

Further, a tomato fruit produced on a plant grown from a seed of NUN 00279 TOP is provided.

In still another aspect, a seed growing or grown on a plant of NUN 00279 TOP is provided (i.e. produced after pollination of the flower of NUN 00279 TOP).

Definitions

All patent and non-patent documents cited herein are incorporated by reference in their entirety "Tomato" refers herein to plants of the species *Solanum lycopersicum*, or a closely related species, and fruits thereof. *Solanum lycopersicum*, is also known as *Lycopersicon lycopersicum* (L.) H. Karst. or *Lycopersicon esculentum* Mill. The most commonly eaten part of a tomato is the fruit or berry. The fruit comprises pericarp, septa, epidermis, columella, locular cavity, vascular bundles and optionally seed. Pericarp, septa, epidermis, columella, locular cavity, vascular bundles, and seedcoat of the seed are maternal tissues, that is they are genetically identical to the plant on which they grow.

"Cultivated tomato" refers to plants of *Solanum lycopersicum*, or a closely related species, i.e. varieties, breeding lines or cultivars of the species *S. lycopersicum* as well as crossbreds thereof, or crossbreds with other *Solanum* species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Solanum* and related species.

"Processing tomato" refers to tomatoes suitable for processing by canning, dicing and pasting.

The terms "tomato NUN 00279 TOP", "NUN 00279 TOP", "NUN 00279", "NUN 00279 F1", "00279 TOP" or "tomato 00279" are used interchangeably herein and refer to a tomato plant of variety NUN 00279 TOP, representative seed of which will be deposited under Accession Number NCIMB 43684.

A "seed of NUN 00279 TOP" refers to a tomato seed which can be grown into a plant of NUN 00279 TOP wherein a representative sample of viable seed of NUN 00279 TOP will be deposited under Accession Number NCIMB 43684. A seed can be in any stage of maturity, for example a mature, viable seed, or an immature, non-viable seed. A seed comprises an embryo and maternal tissues.

An "embryo of NUN 00279 TOP" refers to an "F1 hybrid embryo" as present in a seed of NUN 00279 TOP, a representative sample of said seed of NUN 00279 TOP will be deposited under Accession Number NCIMB 43684.

A "seed grown on NUN 00279 TOP" refers to a seed grown on a mature plant of NUN 00279 TOP or inside a fruit of NUN 00279 TOP. The "seed grown on NUN 00279 TOP" contains tissues and DNA of the maternal parent, NUN 00279 TOP. The "seed grown on NUN 00279 TOP" contains an F2 embryo. When said seed is planted, it grows into a first generation progeny plant of NUN 00279 TOP.

A "fruit of NUN 00279 TOP" refers to a fruit containing maternal tissues of NUN 00279 TOP as deposited under Accession Number NCIMB 43684. In one option, the fruit contains seed grown on NUN 00279 TOP. In another option, the fruit does not contain seed, that is the fruit is parthenocarpic. The skilled person is familiar with methods for inducing parthenocarpy. Those methods comprise chemically or genetically inducing parthenocarpy. Compounds suitable for chemically inducing parthenocarpy comprise auxins, gibberellins and cytokinins. Methods for genetically inducing parthenocarpy comprise the methods described in WO2008143504, WO1998024301, WO1999021411, WO2000074468 and EP142842.

"Tissue culture" refers to a composition comprising isolated cells of the same or a different type or a collection of such cells organized into parts of a plant. Tissue culture of various tissues of tomato and regeneration of plants therefrom is well known and widely published (see, e.g., Bhatia et al. (2004), Plant Cell, Tissue and Organ Culture 78: 1-21. Similarly, the skilled person is well-aware how to prepare a "tissue culture" or "cell culture".

"UPOV descriptors" are the plant variety descriptors described for tomato in the "Guidelines for the Conduct of Tests for Distinctness, Uniformity and Stability, TG/44/10 (Geneva 2011, revised 2013), as published by UPOV (International Union for the Protection of New Varieties and Plants, available on the world wide web at upov.int) and which can be downloaded from the world wide web at upov.int/edocs/tgdocs/en/tg044.pdf and is herein incorporated by reference in its entirety.

"USDA descriptors" are the plant variety descriptors for tomato (*Solanum lycopersicum* or *Lycopersicon esculentum* Mill.) as published by the US Department of Agriculture, Agricultural Marketing Service, Plant Variety Protection Office, Beltsville, Md. 20705 (available on the world wide web at ams.usda.gov) and which can be downloaded from the world wide web at ams.usda.gov/sites/default/files/media/55-Tomato %20ST-470-55%202015.pdf. "Non-USDA descriptors" are other descriptors suitable for describing tomato.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 00279 TOP. An F2 progeny produced from self-pollination of NUN 00279 TOP will thus comprise two sets of chromosomes derived from NUN 00279 TOP, while an F2 progeny derived from cross-fertilization of NUN 00279 TOP will comprise only one set of chromosomes from NUN 00279 TOP and the other set of chromosomes from the other parent.

"Harvested plant material" refers herein to plant parts (e.g. fruits detached from the whole plant) which have been collected for further storage and/or further use.

"Reference Variety" or "check variety" refers herein to variety H 8504, a commercial variety from company Heinz, which has been planted in a trial together with NUN 00279 TOP. USDA descriptors of NUN 00279 were compared to the USDA descriptors of H 8504.

"Rootstock" or "stock" refers to the plant selected for its roots, in particular for the resistance of the roots to diseases or stress (e.g. heat, cold, salinity etc.). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired tomato fruit.

"Stock/scion" or grafted plant refers to a tomato plant comprising a rootstock from one plant grafted to a scion from another plant.

"Grafting" refers to attaching tissue from one plant to another plant so that the vascular tissues of the two tissues join together. Grafting may be done using methods known in the art like: 1) Tongue Approach/Approach Graft, 2) Hole insertion/Terminal/Top Insertion Graft, 3) One Cotyledon/Slant/Splice/Tube Graft and 4) Cleft/Side Insertion Graft.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 00279 TOP may have one or more (or all) of the essential physiological and/or morphological characteristics of said variety listed in Table 1 and/or 2, as determined at the 5% significance level (i.e. $p<0.05$) when grown under the same environmental conditions.

"Distinguishing characteristics" or "distinguishing morphological and/or physiological characteristics" refers herein to the characteristics which distinguish (i.e. are different) between the new variety and other tomato varieties, such as the Reference Variety, when grown under the same environmental conditions. The distinguishing characteristics between NUN 00279 TOP and Reference Variety are described elsewhere herein and also can be seen in Table 1 and/or Table 2. When comparing NUN 00279 TOP with different varieties, the distinguishing characteristics will be different. In one aspect, the distinguishing characteristics may therefore include at least one, two, three or more (or all) of the characteristics listed in Table 1 and/or 2 and/or 3. All numerical distinguishing characteristics are statistically significantly different at $p<0.05$ between NUN 00279 TOP and the other variety, e.g. Reference Variety.

NUN 00279 TOP has the following distinguishing characteristics when compared to the Reference Variety: 1) Average fruit diameter at widest point; 2) Average fruit weight; 3) Typical fruit shape; 4) Average number of flowers in inflorescence; 5) Typical leaf morphology; 6) Average mature plant height; 7) Fruit epidermis type; 8) Average fruit pericarp thickness; 9 Average fruit soluble solids; and 10) Average maturity. This can be seen in a.m. Table 1, where the USDA characteristics of NUN 00279 TOP are compared to the characteristics of Reference Variety, when grown under the same environmental conditions Thus, a tomato plant "comprising the distinguishing characteristics of NUN 00279 TOP (such as a progeny plant)

refers herein to a plant which does not differ significantly from said variety in the distinguishing characteristics above. Therefore in one aspect a plant (such as a progeny plant of NUN 00279 TOP) is provided which does not differ significantly from NUN 00279 TOP in the distinguishing characteristics above.

Similarity and differences between two different plant lines or varieties can be determined by comparing the number of morphological and/or physiological characteristics (e.g. the characteristics as listed in Table 1 and/or 2) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% (p<0.01) or 5% (p<0.05) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated tomato" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all tomato fruits harvested per hectare of a particular line or variety. It is understood that "yield" expressed as weight of all tomato fruits harvested per hectare can be obtained by multiplying the number of plants per hectare times the "yield per plant".

"Marketable yield" means the total weight of all marketable tomato fruits, especially fruit that is not cracked, damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Fruit maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" tomato is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a tomato fruit is ripe or ready for harvest or the optimal time to harvest the fruit for the market, for processing or for consumption. In one embodiment, harvest maturity is the stage which allows proper completion of the normal ripening.

Refractometer % of soluble solids is the percentage of soluble solids in fruit juice, as defined by the USDA. It is also expressed as °Brix and indicates sweetness. The majority of soluble solids in are mainly sugars present in the fruits of. Hence the correlation with sweetness. Brix can be measured using a Brix meter (also known as Refractometer).

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one tomato line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 00279 TOP. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another tomato plant of the same variety or another variety or (breeding) line, or with wild tomato plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration. Thus, a plant of NUN 00279 TOP is the male parent, the female parent or both of a first generation progeny of NUN 00279 TOP. Progeny may have all the physiological and morphological characteristics of variety NUN 00279 TOP when grown under the same environmental conditions and/or progeny may have (be selected for having) one or more of the distinguishing characteristics of tomato of the invention. Using common breeding methods such as backcrossing or recurrent selection, one or more specific characteristics may be introduced into said variety, to provide or a plant comprising all but 1, 2, or 3 or more of the morphological and physiological characteristics of NUN 00279 TOP (as listed in Table 1 and/or 2)

The terms "gene converted" or "conversion plant" or "single locus converted plant" in this context refer to tomato plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of mutation and/or by genetic transformation and/or by backcrossing, wherein essentially all of the desired morphological and physiological characteristics of a tomato variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for tomatoes described herein. The mean, if not indicated otherwise within this application, refers to the arithmetic mean of measurements on at least 10 different, randomly selected plants of a variety or line.

DETAILED DESCRIPTION

The present invention relates to a plant of NUN 00279 TOP wherein a representative sample of seeds of said variety is deposited under the Budapest Treaty, with Accession number NCIMB 43684.

The present invention also relates to a seed of tomato variety, referred to as NUN 00279 TOP, wherein a representative sample of said seed will be deposited under the Budapest Treaty, with Accession number NCIMB 43684.

In another aspect, the invention provides for a tomato plant part of variety NUN 00279 TOP, preferably a fruit, a representative sample of seed from said variety will be deposited under the Budapest Treaty, with Accession number NCIMB 43684.

A seed of hybrid variety NUN 00279 TOP is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 00279 TOP.

Also provided is a plant of tomato variety NUN 00279 TOP, or a fruit or other plant part thereof, produced from a seed, wherein a representative sample of said seeds will be deposited under the Budapest Treaty, with Accession Number NCIMB 43684.

Also a plant part obtained from variety NUN 00279 TOP is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. In a further embodiment, the plant part obtained from variety NUN 00279 TOP is a cell, optionally a cell in a cell or tissue culture. That cell may be grown into a plant of NUN 00279 TOP. A part of a variety of the invention, i.e. NUN 00279 TOP (or of progeny NUN 00279 TOP or of a plant having all physiological and/or morphological characteristics but one, two or three which are different from those of NUN 00279 TOP) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is a tomato fruit or part thereof and/or an extract from a fruit or another plant part described herein comprising at least one cell of NUN 00279 TOP. The food or feed product may be fresh or processed, e.g., dried, grinded, powdered, pickled, chopped, cooked, roasted, in a sauce, in a sandwich, pasted, pured or concentrated, juiced, pickled, canned, steamed, boiled, fried, blanched and/or frozen, etc.

Such a plant part of NUN 00279 TOP can be stored and/or processed further. Encompassed are therefore also food or feed products comprising one or more of such parts, such as canned, chopped, cooked, roasted, in a sauce, in a sandwich, pasted, pured or concentrated, juiced, frozen, dried, pickled, or powdered tomato fruit from NUN 00279 TOP or from progeny of said varieties, or from a derived variety, such as a plant having all but one, two or three physiological and/or morphological characteristics of NUN 00279 TOP.

In a preferred embodiment, the invention provides for a tomato fruit of variety NUN 00279 TOP, or a part of a fruit of said varieties. The fruit can be in any stage of maturity, for example immature or mature. In another embodiment, the invention provides for a container comprising or consisting of a plurality of harvested tomato fruits or parts of fruits of said variety, or fruits of progeny thereof, or fruits of a derived variety.

In another embodiment the plant, plant part or seed of NUN 00279 TOP is inside a container, For example, containers such as cans, boxes, crates, bags, cartons, Modified Atmosphere Packaging, films (e.g. biodegradable films), etc. comprising a plant or a part of a plant (fresh and/or processed) of NUN 00279 TOP or a seed of NUN 00279 TOP are also provided herein. In a preferred embodiment, the container comprises a plurality of seeds of NUN 00279 TOP, or a plurality of plant parts of NUN 00279 TOP.

The present invention further relates to a tomato variety, referred to as NUN 00279 TOP, which—when compared to its REFERENCE VARIETY H 8504—has the following distinguishing characteristics: 1) Average fruit diameter at widest point; 2) Average fruit weight; 3) Typical fruit shape; 4) Average number of flowers in inflorescence; 5) Typical leaf morphology; 6) Average mature plant height; 7) Fruit epidermis type; 8) Average fruit pericarp thickness; 9 Average fruit soluble solids; and 10) Average maturity, where the characteristics are determined at the 5% significance level for plants grown under the same environmental conditions. Also encompassed by the present invention are parts of that plant.

In one embodiment a plant of NUN 00279 TOP or a progeny plant thereof, comprises all of the following morphological and/or physiological characteristics (i.e. average values of distinguishing characteristics, as indicated on the USDA Objective description of variety—tomato (unless indicated otherwise)): 1) Average fruit diameter at widest point; 2) Average fruit weight; 3) Typical fruit shape; 4) Average number of flowers in inflorescence; 5) Typical leaf morphology; 6) Average mature plant height; 7) Fruit epidermis type; 8) Average fruit pericarp thickness; 9 Average fruit soluble solids; and 10) Average maturity, where the characteristics are determined at the 5% significance level for plants grown under the same environmental conditions. An example of values for the distinguishing characteristics collected in a trial run according to UDSA requirements can be found in Table 1. A part of this plant is also provided.

NUN 00279 TOP may further exhibit at least one further trait selected from the group consisting of a) Average fruit stem scar diameter, b) Average Bostwick.

The invention further provides a tomato plant which does not differ from the plant of NUN 00279 TOP as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 00279 TOP. Such a tissue culture can for example be grown on plates or in liquid culture, or be frozen for long term storage. The cells of NUN 00279 TOP used to start the culture can be selected from any plant part suitable for vegetative reproduction, or in a preferred embodiment can be selected from embryos, meristems, cotyledons, hypocotyl, pollen, leaves, anthers, roots, root tips, pistil, petiole, flower, fruit, seed, stem and stalks of NUN 00279 TOP. In another preferred embodiment, the tissue culture does not contain somaclonal variation or has reduced somaclonal variation. The skilled person is familiar with methods to reduce or prevent somaclonal variation, including regular reinitiation.

In one embodiment the invention provides a tomato plant regenerated from the tissue or cell culture of NUN 00279 TOP, wherein the regenerated plant is not significantly different from NUN 00279 TOP in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another embodiment, the invention provides a tomato plant regenerated from the tissue or cell culture of NUN 00279 TOP, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A tomato according to the invention, such as NUN 00279 TOP, or its progeny, or a plant having all physiological and/or morphological characteristics but one, two or three which are different from those of NUN 00279 TOP, can also be reproduced using vegetative reproduction methods. Therefore, the invention provides for a method of producing a plant, or a part thereof, of variety NUN 00279 TOP, comprising vegetative propagation of said variety. Vegetative propagation comprises regenerating a whole plant from a plant part of variety NUN 00279 TOP (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 00279 TOP. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 00279 TOP.

In a preferred embodiment, the part of the plant to be propagated is is a cutting, a cell culture or a tissue culture.

The invention also provides for a vegetatively propagated plant of variety NUN 00279 TOP (or from progeny of said variety or from or a plant having all but one, two or three physiological and/or morphological characteristics of NUN 00279 TOP) wherein the plant has all of the morphological and physiological characteristics of NUN 00279 TOP when the characteristics are determined at the 5% significance level for plants grown under the same conditions. In another embodiment, the propagated plant has all but one, two or three of the morphological and physiological characteristics of NUN 00279 TOP when the characteristics are determined at the 5% significance level for plants grown under the same conditions. A part of said propagated plant or said propagated plant with one, two or three differences is also included.

In an embodiment, the invention provides a method for producing a tomato plant part, preferably a fruit, comprising the steps of:
  a. Growing a plant of NUN 00279 TOP until it sets at least one fruit
  b. Collecting the fruit of step a)

Preferably, the fruit is collected at harvest maturity. In another embodiment, the fruit is collected when the seed is ripe. A plant of NUN 00279 TOP can be produced by seeding directly in the soil (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the tomato seed may be planted through a black plastic mulch. The dark plastic will absorb heat from the sun, warming the soil early. It will also help to conserve moisture during the growing season, controls weeds and makes harvesting easier and cleaner. Tomato can also be grown entirely in greenhouses. See for example: M Domis, A P Papadopoulos (2002) Horticultural Reviews for cultivation, harvesting, handling and postharvest methods commonly used In still another aspect the invention provides a method of producing a tomato plant, comprising crossing a plant of tomato NUN 00279 TOP with a second tomato plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent tomato plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 00279 TOP one or more times, and selecting a progeny plant from said selfing. In one aspect the progeny plant retains all the distinguishing characteristics of NUN 00279 TOP described above. In a different embodiment the progeny plant comprises all (or all but one, two or three) of the physiological and morphological characteristic of NUN 00279 TOP of Table 1, and/or Table 2. In a further embodiment the progeny plant comprises all physiological and morphological characteristic of NUN 00279 TOP when grown under the same environmental conditions.

In other aspects, the invention provides a progeny plant of variety NUN 00279 TOP such as a progeny plant obtained by further breeding that variety. Further breeding with the variety of the invention includes selfing that variety one or more times and/or cross-pollinating that variety with another tomato plant or variety one or more times. In particular, the invention provides for a progeny plant that retains all the essential morphological and physiological characteristics of NUN 00279 TOP or, in another embodiment, a progeny plant that retains all, or all but one, two or three, of the morphological and physiological characteristics of NUN 00279 TOP, optionally all or all but one, two or three of the characteristics as listed in Table 1 and/or 2, when grown under the same environmental conditions, determined at the 5% significance level for numerical characteristics. In a preferred embodiment, the progeny is a first generation progeny, i.e. the ovule or the pollen (or both) used in the crossing is an ovule or pollen of variety NUN 00279 TOP, i.e. the pollen comes from an anther of NUN 00279 TOP and the ovule comes from an ovary of NUN 00279 TOP. In another aspect, the invention provides for a vegetative reproduction of the variety and a plant having all, or all but 1, 2, or 3 of the physiological and morphological characteristics of NUN 00279 TOP (e.g. as listed in Table 1 and/or 2).

The invention also provides a method for collecting pollen of NUN 00279 TOP, comprising the steps of:

a. Growing a plant of NUN 00279 TOP until at least one flower contains pollen
b. Collecting the pollen of step a)

Preferably, the pollen is collected when it is mature or ripe. A suitable method for collecting pollen comprises collecting anthers or the part of the anther that contains pollen, for example by cutting it off. Pollen can be collected in containers. Optionally, collected pollen can be used to pollinate a tomato flower.

The morphological and/or physiological differences between two different individual plants of the invention (e.g. between NUN 00279 TOP and a progeny of NUN 00279 TOP) or between a plant of NUN 00279 TOP or progeny of said variety, or a plant having all, or all but 1, 2, or 3, of the physiological and morphological characteristics of NUN 00279 TOP (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said tomato cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of tomato. Thus, the invention comprises tomato plant having one, two or three physiological and/or morphological characteristics which are different from those of the plant of NUN 00279 TOP and which otherwise has all the physiological and morphological characteristics of the plant of NUN 00279 TOP, when determined at the 5% significance level for plants grown under the same environmental conditions. In a preferred embodiment, the different characteristic is affected by a mutation, optionally induced mutation, or by transformation.

The morphological and physiological characteristics (and the distinguishing characteristics) of NUN 00279 TOP are provided in the Examples, in Table 1 and/or 2. Encompassed herein is also a plant obtainable from NUN 00279 TOP (e.g. by selfing and/or crossing and/or backcrossing with said variety and/or progeny of said variety) comprising all or all but one, two or three of the physiological and morphological characteristics of NUN 00279 TOP listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of fruits can be compared, such as cold storage holding quality, post-harvest flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In yet a further embodiment, the invention provides for a method of producing a new tomato plant. The method comprises crossing a plant of the invention i.e. NUN 00279 TOP, or a plant comprising all but 1, 2, or 3 of the morphological and physiological characteristics of said variety (as listed in Table 1 and/or 2), or a progeny plant thereof, either as male or as female parent, with a second tomato plant (or a wild relative of tomato) one or more times, and/or selfing a tomato plant according to the invention i.e. NUN 00279 TOP, or a progeny plant thereof, one or more times, and selecting progeny from said crossing and/or selfing. The second tomato plant may for example be a line or variety of the species *Solanum Lycopersicon, S. chilense, S. habrochaites, S. penelli, S. peruvianum, S. pimpinellifolium* or other *Solanum* species.

The invention provides for methods of producing plants which retain all the morphological and physiological characteristics of a plant of the invention i.e. NUN 00279 TOP. The invention provides also for methods of producing a plant comprising all but 1, 2, or 3 or more of the morphological and physiological characteristics of NUN 00279 TOP (e.g. as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 00279 TOP if its DNA fingerprint is at least 80%, 90%, 95% or 98% identical to the fingerprint of NUN 00279 TOP. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Ince et al., (2010) Biochem. Genet. 48:83-95).

The invention also provides a plant and a variety obtained or selected by applying these methods on NUN 00279 TOP. Such a plant may be produced by crossing and/or selfing, or alternatively, a plant may simply be identified and selected amongst plants of said variety, or progeny of said variety, e.g. by identifying a variant within NUN 00279 TOP or within progeny of said variety (e.g. produced by selfing) which variant differs from NUN 00279 TOP in one, two or three of the morphological and/or physiological characteristics (e.g. in one, two or three distinguishing characteristics), e.g. those listed in Table 1 and/or 2 or others. In one embodiment the invention provides a tomato plant having a Jaccard's Similarity index with NUN 00279 TOP of at least 0.8, e.g. at least 0.85, 0.9, 0.95, 0.98 or even at least 0.99.

WO2013182646, which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 00279 TOP is a progeny of said variety, because the seed coat of the seed is a maternal tissue genetically identical to NUN 00279 TOP. In one embodiment, the present invention relates to a seed coat comprising maternal tissue of NUN 00279 TOP. In another embodiment the invention relates to a tomato seed comprising a maternal tissue of NUN 00279 TOP.

By crossing and/or selfing also (one or more) single traits may be introduced into the variety of the invention i.e. NUN 00279 TOP (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 00279 TOP by breeding with said variety.

Alternatively, a single trait converted plant or single locus converted plant of NUN 00279 TOP may be produced by the following steps
  a. obtaining a cell or tissue culture of cells of NUN 00279 TOP;
  b. genetically transforming or mutating said cells;
  c. growing the cells into a plant; and
  d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 00279 TOP, progeny of said variety or into a plant comprising all but 1, 2, or 3 or more of the morphological and physiological characteristics of NUN 00279 TOP (e.g. as listed in Table 1). Resistance to one or more of the following diseases or pests is preferably introduced into plants of the invention: Tomato Mosaic Virus, Curly Top Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), *Alternaria*, Bacterial Spot (*Xanthomonas vesicatoria*), Nematode (*Meloidogyne* spp), Late blight (*Phytophthora infestans* races), Leaf mold (*Cladosporium fulvum* races), Colorado potato beetle, Spider mites, Whitefly and *Verticillium* Wilt (*Verticillium dahliae*). Other resistance genes, against pathogenic viruses, fungi, bacteria, nematodes, insects or other pests may also be introduced.

Thus, invention also provides a method for developing a tomato plant in a tomato breeding program, using a tomato plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 00279 TOP or progeny of said variety, or a plant comprising all but 1, 2, or 3 or more of the morphological and physiological characteristics of NUN 00279 TOP (e.g. as listed in Table 1 and/or 2), with a different tomato plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Vidavsky and Czosnek, (1998) Phytopathology 88(9): 910-4). For breeding methods in general see Principles of Plant Genetics and Breeding, 2007, George Acquaah, Blackwell Publishing, ISBN-13: 978-1-4051-3646-4.

The invention also provides a tomato plant comprising at least a first set of the chromosomes of tomato variety NUN 00279 TOP, a sample of seed of said variety will be deposited under Accession Number NCIMB 43684; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 00279 TOP may also be mutated (by e.g. irradiation, chemical mutagenesis, heat treatment, etc.) and mutated seeds or plants may be selected in order to change one or more characteristics of said variety. Methods such as TILLING may be applied to tomato populations in order to identify mutants. Similarly, NUN 00279 TOP may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 00279 TOP, or progeny of said variety, by transforming said variety or progeny of said variety with a transgene that confers the desired trait, wherein the transformed plant retains all or all but one, two or three of the phenotypic and/or morphological and/or physiological characteristics of NUN 00279 TOP or the progeny of said variety and contains the desired trait.

The invention also provides a plant or a cell of a plant comprising a desired trait produced by mutating a plant of variety NUN 00279 TOP or a cell thereof and selecting a plant the desired trait, wherein the mutated plant retains all or all but one of the phenotypic and morphological characteristics of said variety, optionally as described for each variety in in Table 1 and/or 2, and contains the desired trait and wherein a representative sample of seed of variety NUN 00279 TOP to be deposited under Accession Number NCIMB 43684. In a further embodiment, the desired trait is selected from the group consisting of yield, storage properties, color, flavor, male sterility, herbicide tolerance, insect resistance, pest resistance, disease resistance, environmental stress tolerance, modified carbohydrate metabolism, modified protein metabolism and ripening or the mutation occurs in any of the following genes acs2, acs4, rin, pp2c1, arf9, intense, myb12.

A suitable method for inducing mutation in NUN 00279 TOP comprises the steps of:

a. Exposing a seed, a plant or a plant part or a cell of NUN 00279 TOP to a mutagenic compound or to radiation, wherein a representative sample of seed of NUN 00279 TOP is deposited under Accession Number NCIMB 43684, b. Selecting a seed, a plant or a plant part or a cell of NUN 00279 TOP having a mutation c. Optionally growing and/or multiplying the seed, plant or plant part or cell of NUN 00279 TOP having the mutation.

The invention also provides a plant having one, two or three physiological and/or morphological characteristics which are different from those of NUN 00279 TOP and which otherwise has all the physiological and morphological characteristics of said variety, wherein a representative sample of seed of variety NUN 00279 TOP will be deposited under Accession Number NCIMB 43684. In particular variants which differ from NUN 00279 TOP in none, one, two or three of the characteristics mentioned in Table 1 and/or 2 are encompassed.

A part of a variety of the invention, i.e. NUN 00279 TOP (or of progeny of said varieties or of a plant having all physiological and/or morphological characteristics but one, two or three which are different from those of said variety) encompasses any cells, tissues, organs obtainable from the seedlings or plants, such as but not limited to: a tomato fruit or a part thereof, a cutting, hypocotyl, cotyledon, seed coat, pollen and the like. Such parts can be stored and/or processed further. Encompassed are therefore also food or feed products comprising a part of NUN 00279 TOP or a part of progeny of said varieties, or a part of a plant having all but one, two or three physiological and/or morphological characteristics of NUN 00279 TOP, comprising one or more of such parts, optionally processed (such as canned, chopped, cooked, roasted, in a sauce, in a sandwich, pasted, pured or concentrated, juiced, frozen, dried, pickled, or powdered).

In one aspect a haploid plant and/or a doubled haploid plant of NUN 00279 TOP, or of a plant having all but one, two or three physiological and/or morphological characteristics of NUN 00279 TOP, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or doubled haploid plants derived from NUN 00279 TOP that, when combined, make a set of parents of NUN 00279 TOP are encompassed herein. Thus the haploid plant and/or the doubled haploid plant of NUN 00279 TOP can be used in a method for generating parental lines of NUN 00279 TOP.

Using methods known in the art like "reverse synthesis of breeding lines" or "reverse breeding", it is possible to produce parental lines for a hybrid plant such as NUN 00279 TOP; where normally the hybrid is produced from the parental lines. Thus, this method introduces a tool that was not available in traditional breeding: a skilled person can take any individual heterozygous plant (called a "phenotypically superior plant" in Example 2 of WO2014076249; NUN 00279 TOP is such a plant) and generate a combination of parental lines (reverse breeding parental lines) that, when crossed, produce the variety NUN 00279 TOP. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al., Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 00279 TOP) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 00279 TOP when these parental lines are crossed. In still another aspect, the invention relates to a combination of parental lines from which a seed or plant having all physiological and/or morphological characteristics of NUN 00279 TOP (when the characteristics are determined at the 5% significance level for plants grown under the same conditions).

In another aspect, the invention comprises a method for making doubled haploid cells from haploid cells of NUN 00279 TOP according to various methods known to the skilled person. A suitable method is colchicine treatment.

In another alternative aspect, the invention provides a method of introducing a single locus conversion or single trait conversion or a desired trait into NUN 00279 TOP comprising:
  a. obtain a combination of a parental lines of NUN 00279 TOP, optionally through reverse synthesis of breeding lines,
  b. introduce a single locus conversion in at least one of the parents of step a;
  c. crossing the converted parent with the other parent of step a to obtain seed of NUN 00279 TOP A combination of a male and a female parental line of NUN 00279 TOP can be generated by methods described herein, for example through reverse synthesis of breeding lines.

In an embodiment of the invention, Step b) of the above method—introduce a single locus conversion in at least one of the parents of step a—may be done through the following method:
  i. obtaining a cell or tissue culture of cells of the parental line of NUN 00279 TOP;
  ii. genetically transforming or mutating said cells;
  iii. growing the cells into a plant; and
  iv. optionally selecting plants that contain the single locus conversion, the single trait conversion or the desired trait.

In another embodiment of the invention, Step b) of the above method—introduce a single locus conversion in at least one of the parents of step a—may also be done through the following method:
  i. crossing the parental line of NUN 00279 TOP with a second tomato plant comprising the single locus conversion, the single trait conversion or the desired trait;
  ii. selecting F1 progeny plants that contain the single locus conversion, the single trait conversion or the desired trait;
  iii. crossing said selected progeny plants of step ii with the parental line of step i, to produce a backcross progeny plant;
  iv. selecting backcross progeny plants comprising the single locus conversion, the single trait conversion or the desired trait and otherwise all or all but one, two or three of the morphological and physiological characteristics the parental line of step i to produce selected backcross progeny plants; and
  v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to Tomato Mosaic Virus, Curly Top Virus, Tomato Mottle Virus, Potato Y Virus, Blotchey Ripening, Tobacco Etch Virus, the various Tobacco Mosaic Virus races, Concentric cracking, Tomato spotted wilt, Tomato yellows, Gold Fleck, Bacterial canker, Bacterial soft rot, Bacterial speck, Bacterial wilt, Anthracnose (*Gloeosporium piperatum*), *Fusarium* wilt (*F. oxysporum* races), *Alternaria*, Bacterial Spot (*Xanthomonas vesicatoria*), Nematode (*Meloidogyne* spp), Late blight (*Phytophthora infestans* races), Leaf mold (*Cladosporium fulvum* races), Colorado potato beetle, Spider mites, Whitefly and *Verticillium* Wilt (*Verticillium dahliae*). Other resistance genes, against pathogenic viruses, fungi, bacteria, nematodes, insects or other pests may also be introduced.

Thus, the invention also provides a combination of parental lines which, when crossed, produce a seed or plant having all physiological and/or morphological characteristics of NUN 00279 TOP but one, two or three which are different (when grown under the same environmental conditions), as well as a seed or plant having all physiological and/or morphological characteristics of NUN 00279 TOP but one, two or three which are different (when the characteristics are determined at the 5% significance level for plants grown under the same conditions).

Also provided is a plant part obtainable from variety NUN 00279 TOP or from progeny of said variety or from a plant having all but one, two or three physiological and/or morphological characteristics which are different from those of NUN 00279 TOP, or from a vegetatively propagated plant of NUN 00279 TOP (or from its progeny or from a plant having all or all but one, two or three physiological and/or morphological characteristics which are different from those of NUN 00279 TOP), being selected from the group consisting of a fruit, a harvested fruit, a part of a fruit, a leaf, a part of a leaf, pollen, an ovule, a cell, a petiole, a shoot or a part thereof, a stem or a part thereof, a root or a part thereof, a root tip, a seed, a part of a seed, seed-coat or another maternal tissue which is part of a seed grown on NUN 00279 TOP, or hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a tomato fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, pured or concentrated, juiced, pickled, canned, steamed, boiled, fried, blanched and/or frozen, etc.

Marketable tomato fruits are generally sorted by size and quality after harvest. Alternatively the tomato fruits can be sorted by expected shelf life, pH or Brix.

Tomatoes may also be grown for use as rootstocks (stocks) or scions (cions). Typically, different types of tomatoes are grafted to enhance disease resistance, which is usually conferred by the rootstock, while retaining the horticultural qualities usually conferred by the scion. It is not uncommon for grafting to occur between cultivated tomato varieties and related species. Methods of grafting and vegetative propagation are well-known in the art.

So in one aspect the invention relates to a plant comprising a rootstock or scion of NUN 00279 TOP.

All documents (e.g., patent publications) are herein incorporated by reference in their entirety. Cited references:
WO1998024301
WO1999021411
WO2000074468
WO2008143504
WO2013182646
WO2014076249
EP142842
Acquaah, Principles of Plant Genetics and Breeding, 2007, Blackwell Publishing, ISBN-13: 978-1-4051-3646-4.
Bhatia et al. (2004), Plant Cell, Tissue and Organ Culture 78: 1-21.
Vidavsky and Czosnek, (1998) Phytopathology 88(9): 910-4)
Vos et al. 1995, Nucleic Acid Research 23: 4407-4414
Wijnker et al., Nature Protocols Volume: 9, Pages: 761-772 (2014) DOI: doi: 10.1038/nprot.2014.049,
FAOSTAT 2012
RHS color chart: 2007 (The Royal Horticultural Society, charity No: 222879, PO Box 313 London SW1P2PE.
UPOV Guidelines for the Conduct of Tests for Distinctness, Uniformity and Stability, TG/44/10 (Geneva 2011, revised 2013 upov.int/edocs/tgdocs/en/tg044.pdf
USDA descriptors *Solanum lycopersicum* or *Lycopersicon esculentum* Mill.) US Department of Agriculture, Agricultural Marketing Service, Plant Variety Protection Office, Beltsville, Md. 20705 ams.usda.gov/sites/default/files/media/55-Tomato%20ST-470-55%202015.pdf.

EXAMPLES

Development of NUN 00279 TOP

The hybrid NUN 00279 TOP was developed from a male and female proprietary inbred line of Nunhems. The female and male parents were crossed to produce hybrid (F1) seeds of NUN 00279 TOP The seeds of NUN 00279 TOP can be grown to produce hybrid plants and parts thereof (e.g. tomato fruit). The hybrid NUN 00279 TOP can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 00279 TOP is uniform and stable.

DEPOSIT INFORMATION

A total of 2500 seeds of the hybrid variety NUN 00279 TOP have been deposited and accepted according to the Budapest Treaty by Nunhems B.V. on Nov. 6, 2020, at the NCIMB Ltd., Ferguson Building, Craibstone Estate, Bucksburn, Aberdeen AB21 9YA, United Kingdom (NCIMB). The deposit has been assigned NCIMB number 43684. A deposit of NUN 00279 TOP and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 00279 TOP is referred to as Reference Variety, a variety from Heinz with the commercial name H 8504. In Table 1 a comparison between NUN 00279 TOP and the Reference Variety will be shown based on a trial in the USA during the trial season 2018. Trial location: Acampo, Calif., USA (38.192873° N, 121.232637° W), transplanting date: Jun. 8, 2017, harvesting date: Sep. 25, 2017.

A trial of 40 plants of each variety, from which at least 15 plants or plant parts were randomly selected, will be used to measure characteristics. For numerical characteristics averages will be calculated. For non-numerical characteristics the type/degree will be determined. In Table 1 the USDA descriptors of NUN 00279 TOP (this application) and the Reference Variety (commercial variety) are listed, which will be measured in the trial to be performed.

In accordance with one aspect of the present invention, there is provided a plant having the physiological and morphological characteristics of NUN 00279 TOP as will be presented in Table 1.

TABLE 1

| Objective description of varieties NUN 00279 TOP and Reference Variety | | |
|---|---|---|
| USDA descriptor | Application variety NUN 00279 TOP | Reference variety H 8504 |
| Seedling: | | |
| Anthocyanin in hypocotyl of 2-15 cm: 1 = absent; 2 = present | 2 | 2 |
| Habit of 3-4 week old seedling: 1 = normal; 2 = compact | 1 | 1 |
| Mature plant: | | |
| Height (cm) | 64.2 | 73.3 |
| Growth type: 1 = indeterminate; 2 = determinate | 2 | 2 |
| Form: 1 = lax; 2 = normal; 3 = compact; 4 = dwarf; 5 = brachytic | 2 | 2 |
| Size of canopy (compared to others of similar form): 1 = small; 2 = medium; 3 = large | 2 | 2 |
| Habit: 1 = sprawling; 2 = semi-erect; 3 = erect (Dwarf Champion) | 2 | 2 |
| Stem: | | |
| Branching: 1 = sparse (Brehm's Solid Red; Fireball); 2 = intermediate (Westover); 3 = profuse (UC 82) | 3 | 3 |
| Branching at cotyledon or first leafy node: 1 = present; 2 = absent | 2 | 2 |
| Number of nodes between first inflorescence: 1 = 1-4; 2 = 4-7; 3 = 7-10; 4 = 10 or more | n.r. | n.r. |
| Number of nodes between early ($1^{st}$ to $2^{nd}$, $2^{nd}$ to $3^{rd}$) inflorescences | 2.3 | 2.1 |
| Number of nodes between later developing inflorescences | 1.9 | 1.3 |
| Pubescence on younger stems: 1 = smooth (no long hairs); 2 = sparsely hairy (scattered long hairs); 3 = moderately hairy; 4 = densely hairy or wooly | 2 | 2 |
| Leaf: | | |
| Type: 1 = tomato; 2 = potato (Trip-L-Crop) | 1 | 1 |
| Margins of major leaflets: 1 = absent; 2 = shallowly toothed or scalloped; 3 = deeply toothed or cut, sps. towards base | 2 | 2 |
| Marginal rolling or wiltiness: 1 = absent; 2 = slight; 3 = moderate; 4 = strong | 1 | 1 |
| Onset of leaflet rolling: 1 = early-season; 2 = mid-season; 3 = late-season | 3 | 3 |
| Surface of major leaflets: 1 = smooth; 2 = rugose (bumpy or veiny) | 1 | 1 |
| Pubescence: 1 = smooth (no long hairs); 2 = normal; 3 = hirsute; 4 = wooly | 2 | 2 |
| Inflorescence: | | |
| Type: 1 = simple; 2 = forked (2 major axes); 3 = compound (much branched) | 1 | 1 |
| Number of flowers in inflorescence average | 9.86 | 5.73 |
| Leafy or "running" inflorescence: 1 = absent; 2 = occasional; 3 = frequent | 2 | 1 |
| Flower: | | |
| Calyx: 1 = normal, lobes awl-shaped; 2 = macrocalyx, lobes large, leaflike; 3 = fleshy | 1 | 1 |
| Calyx-lobes: 1 = shorter the corolla; 2 = approx., equaling corolla; 3 = distinctly longer than corolla | 1 | 1 |
| Corolla color: 1 = yellow: 2 = old gold; 3 = white or tan | 1 | 1 |
| Style pubescence: 1 = absent; 2 = sparse; 3 = dense | 1 | 1 |
| Anthers: 1 = all fused into tube; 2 = separating into 2 or more groups at anthesis | 1 | 1 |
| Fasciation (1st flower of 2nd or $3^{rd}$ inflorescence): 1 = absent; 2 = occasionally present; 3 = frequently present | 3 | 3 |

TABLE 1-continued

Objective description of varieties NUN 00279 TOP and Reference Variety

| USDA descriptor | Application variety NUN 00279 TOP | Reference variety H 8504 |
|---|---|---|
| Fruit: | | |
| Typical fruit shape (match illustration) | 7 (ovate) | 9 (cylindrical) |
| Shape of transverse section: 1 = round; 2 = flattened; 3 = angular; 4 = irregular | 1 | 1 |
| Shape of stem end: 1 = flat; 2 = indented | 1 | 1 |
| Shape of blossom end: 1 = indented; 2 - flat; 3 = nippled; 4 - tapered | 3 | 3 |
| Shape of pistil scar: 1 = dot; 2 = stellate; 3 = linear; 4 = irregular | 1 | 1 |
| Abscission layer: 1 = present (pedicellate); 2 = absent (jointless) | 2 | 2 |
| Point of detachment of fruit at harvest: 1 = at pedicel joint; 2 = at calyx attachment | 2 | 2 |
| Length of pedicel (from joint to calyx attachment) (mm) | 22.2 | 22.8 |
| Length of mature fruit (stem axis) (mm) | 57.41 | 62.18 |
| Diameter of fruit at widest point (mm) | 42.58 | 44.24 |
| Weight of mature fruit (gram) | 55.46 | 65.33 |
| Number of locules: 1 = two; 2 = three or four; 3 = five or more | 1 | 1 |
| Fruit surface: 1 = smooth; 2 = slightly rough; 3 = moderately rough or ribbed | 1 | 1 |
| Fruit base color (mature-green stage): 1 = light green (Lanai; VF 145-F5); 2 = light gray-green; 3 = apple or medium green (Heinz 1439 VF); 4 = yellow green; 5 = dark green (RHS color code) | 4 (RHS 144B) | 2 (RHS 145A) |
| Fruit pattern (mature-green stage): 1 = uniform green; 2 = green-shouldered; 3 = radial stripes on sides of fruit | 1 | 1 |
| Shoulder color if different from base: 1 = dark green; 2 = grey green; 3 - yellow green | n.r. | n.r. |
| Fruit color hill ripe: 1 = white; 2 = yellow; 3 = orange; 4 = pink; 5 = red; 6 = brownish; 7 = greenish; 8 = other | 5 (RHS N34A) | 5 (RHS 34B) |
| Flesh color full ripe: 1 = yellow; 2 = pink; 3 = red/crimson; 4 = orange; 5 other | 3 (RHS 45B) | 3 (RHS 45A) |
| Flesh color: 1 = uniform; 2 = with lighter and darker areas in walls | 1 | 1 |
| Locular gel color of table-ripe fruit 1 = green; 2 = yellow; 3 = red | 3 | 3 |
| Ripening: 1 = blossom to stem end; 2 = uniform | 2 | 2 |
| Ripening: 1 = inside out; 2 = uniformity; 3 = outside in | 2 | 2 |
| Stem scar size: 1 = small (Roma); 2 = medium (Rutgers); 3 = large | 1 | 1 |
| Core: 1 = coreless (absent or smaller than 6 × 6 mm); 2 = present | 1 | 1 |
| Epidermis color: 1 = colorless; 2 = yellow | 1 | 1 |
| Epidermis: 1 = normal; 2 = easy-peel | 1 | 2 |
| Epidermis texture: 1 = tender; 2 = average; 3 = tough | 3 | 3 |
| thickness of pericarp (mm): | 5.7 | 5.2 |
| Chemistry and composition of full-ripe fruits: | | |
| pH | 4.54 | 4.31 |
| Titratable acidity as % citric | 1.03 | 1.31 |
| Total solids | n.r. | n.r. |
| Soluble solids as Brix | 7.4 | 7.0 |
| Phenology: | | |
| Seeding to 50% growth (1 open on 50% of plants) | n.r. | n.r. |
| Seed to once over harvest (days) | 126 | 130 |
| Fruit season: 1 = long (Marglobe); 2 = medium (Westover); 3 = short, concentrated (VF 145); 4 = very concentrated (UC82) | 4 | 4 |
| Relative maturity in areas tested: 1 = early; 2 = medium early; 3 = medium; 4 - medium late; 5 = late; 6 = variable | 2 | 3 |
| Adaptation: | | |
| Culture: 1 = field; 2 = greenhouse | 1 | 1 |
| Principle use(s): 1 = home garden; 2 = fresh market; 3 = wholepack canning; 4 = concentrated products 5 = other: Dice | 4 | 4 |
| Machine harvest: 1 = not adapted; 2 = adapted | 2 | 2 |
| Regions to which adaptation has been demonstrated: 1 = Northeast; 2 = Mid Atlantic; 3 = Southeast; 4 Florida; 5 = Great Plains, 6 = south central; 7 = Intermountain West; 8 = Northwest; 9 = California (Sacramento and Upper San Joaquin Valley); 10 = California (Coastal Areas); 11 California (Southern San Joaquin Valley & desserts) | 9, 11 | 9, 11 |

TABLE 2

| Non-USDA descriptor | Application variety NUN 00279 TOP | Reference variety H 8504 |
|---|---|---|
| Plant spread (cm): | 86.76 | 90.6 |
| Stem length between $1^{st}$ and $2^{nd}$ clusters (mm) | 142.53 | 148.8 |
| Stem length between $2^{nd}$ and $3^{rd}$ clusters (mm) | 106.79 | 97.95 |
| Leaf length (cm) | 26.6 | 25.6 |
| Leaf width (cm) | 17.83 | 19.73 |
| Fruit stem scar diameter (mm) | 5.27 | 6.61 |
| Pedicel diameter (mm) | 2.8 | 2.93 |
| Number of locules | 2.6 | 2.3 |
| Bostwick | 12.13 | 12.96 |

Table 1 and 2 contain typical values. Values may vary due to environment. Other values that are substantially equivalent are also within the scope of the invention. N.A.=not applicable; n.r.=not recorded.

What is claimed is:

1. A plant, a plant part or a seed of tomato variety NUN 00279 TOP, wherein a representative sample of seed of said variety is deposited under Accession Number NCIMB 43684.

2. The plant part of claim 1, wherein the plant part is a leaf, pollen, an ovule, a fruit, a scion, a root, a rootstock, a cutting, a flower, or a cell.

3. A seed that produces the plant of claim 1.

4. A tomato plant or a part thereof having all of the physiological and morphological characteristics of the plant of claim 1.

5. A tomato plant or a part thereof which does not differ from the plant of claim 1, in any of the characteristics [listed in Tables 1 and 2] of tomato variety NUN 00279 TOP, when the characteristics are determined at the 5% significance level when grown under the same environmental conditions, and wherein a representative sample of seed of tomato variety NUN 00279 TOP is deposited under Accession Number NCIMB 43684.

6. A tissue or cell culture comprising regenerable cells of the plant of claim 1.

7. The tissue or cell culture according to claim 6, comprising cells or protoplasts obtained from a plant part suitable for vegetative reproduction, wherein the plant part is a meristem, a cotyledon, a hypocotyl, pollen, a leaf, an anther, a root, a root tip, a pistil, a petiole, a flower, a fruit, a stem, or a stalk.

8. A tomato plant regenerated from the tissue or cell culture of claim 6, wherein the plant has all of the physiological and morphological characteristics of the plant of variety NUN 00279 TOP, when the characteristics are determined at the 5% significance level for plants grown under the same environmental conditions, and wherein a representative sample of seed of tomato variety NUN 00279 TOP is deposited under Accession Number NCIMB 43684.

9. A method of producing the plant of claim 1, or a part thereof, comprising vegetative propagating at least a part of the plant of variety NUN 00279 TOP, wherein a representative sample of seed of said variety is deposited under Accession Number NCIMB 43684.

10. The method of claim 9, wherein said vegetative propagating comprises regenerating a whole plant from said part of the plant of variety NUN 00279 TOP, and wherein a representative sample of seed of said variety is deposited under Accession Number NCIMB 43684.

11. The method of claim 9, wherein said part is a cutting, a cell culture or a tissue culture.

12. A vegetative propagated plant, or a part thereof produced by the method of claim 9, wherein the vegetative propagated plant and part thereof have all of the physiological and morphological characteristics of the plant of variety NUN 00279 TOP, when the characteristics are determined at the 5% significance level for plants grown under the same environmental conditions, and wherein a representative sample of seed of tomato variety NUN 00279 TOP is deposited under Accession Number NCIMB 43684.

13. A method of producing a tomato seed, comprising crossing the plant of claim 1 with a second tomato plant at least once, selecting a progeny tomato plant from said crossing and allowing the progeny to form seed.

14. A tomato plant having all the physiological and morphological characteristics of the plant of claim 1, when determined at the 5% significance level for plants grown under the same environmental conditions, wherein a representative sample of seed of tomato variety NUN 00279 TOP is deposited under Accession Number NCIMB 43684, further comprising a transgene.

15. A plant of tomato variety NUN 00279 TOP having all of the morphological and physiological characteristics of the plant of claim 1, wherein a representative sample of seed of said variety is deposited under Accession Number NCIMB 43684, when said characteristics are determined at the 5% significance level for plants grown under the same environmental conditions, further comprising a single locus conversion, optionally wherein the single locus conversion confers male sterility, herbicide tolerance, insect resistance, pest resistance, disease resistance, environmental stress tolerance, modified carbohydrate metabolism, or modified protein metabolism.

16. A method of producing doubled haploids of tomato variety NUN 00279 TOP, comprising making doubled haploid cells from haploid cells from the plant or plant part of claim 1, wherein a representative sample of seed of tomato variety NUN 00279 TOP is deposited under Accession Number NCIMB 43684.

17. A plant comprising the scion or rootstock of claim 2.

18. A container comprising the plant, plant part or seed of claim 1.

19. A method of producing a tomato fruit, comprising:
 a. growing the plant of claim 1 until it sets at least one fruit; and
 b. collecting the fruit of step a).

20. A method of collecting pollen of tomato variety NUN 00279 TOP comprising:
 a. growing the plant of claim 1 until at least one flower contains pollen; and
 b. collecting the pollen of step a).

* * * * *